United States Patent
Parrill-Baker et al.

(10) Patent No.: US 8,497,371 B2
(45) Date of Patent: Jul. 30, 2013

(54) PIPEMIDIC ACID DERIVATIVE AUTOTAXIN INHIBITORS

(75) Inventors: Abby Louise Parrill-Baker, Memphis, TN (US); Daniel Lee Baker, Memphis, TN (US); Adrienne Hoeglund, Collierville, TN (US)

(73) Assignee: University of Memphis Research Foundation, Memphis, TN (US)

( * ) Notice: Subject to any disclaimer, the term of this patent is extended or adjusted under 35 U.S.C. 154(b) by 0 days.

(21) Appl. No.: 12/912,604

(22) Filed: Oct. 26, 2010

(65) Prior Publication Data

US 2012/0100592 A1    Apr. 26, 2012

Related U.S. Application Data

(60) Provisional application No. 61/254,981, filed on Oct. 26, 2009.

(51) Int. Cl.
*C07D 471/04* (2006.01)

(52) U.S. Cl.
USPC ............................................ 544/279

(58) Field of Classification Search
USPC .......................................................... 544/279
See application file for complete search history.

(56) References Cited

PUBLICATIONS

Parrill et al. (Bioorganic & Medicinal Chemistry (2008), 16(4), 1784-1795).*

* cited by examiner

*Primary Examiner* — Bruck Kifle
(74) *Attorney, Agent, or Firm* — Wyatt, Tarrant & Combs, LLP; William S. Parks

(57) ABSTRACT

Novel and optimized classes of pipemidic acid derivative compounds that exhibit effective inhibition of autotaxin enzymes are provided. Such classes of compounds exhibit exhibit reactivity with autotaxin to ultimately reduce the size of the reactive sites thereon to prevent conversion of lysophosphatidyl choline to lysophophatidic acid. Furthermore, such compounds can be incorporated within delivery forms for human ingestion. As such, these compounds accord an excellent manner of potentially reducing generation of certain cancers attributable to the presence of naturally occurring autotaxin within the human body. Methods of inactivating autotaxin to certain degrees therewith such compounds are encompassed within invention as well.

13 Claims, 4 Drawing Sheets

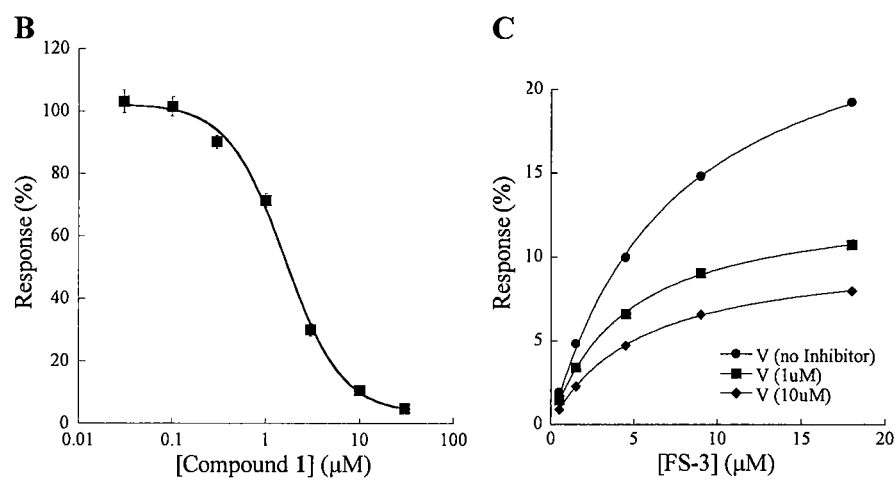
Figure 1                    Figure 2

PIPEMIDIC ACID DERIVATIVE AUTOTAXIN INHIBITORS

This application claims priority from U.S. Provisional Patent Application No. 61/254,981, filed on Oct. 26, 2009.

FIELD OF THE INVENTION

Novel and optimized classes of pipemidic acid derivative compounds that exhibit effective inhibition of autotaxin enzymes are provided. Such classes of compounds exhibit reactivity with autotaxin to ultimately reduce the size of the reactive sites thereon to prevent conversion of lysophosphatidyl choline to lysophophatidic acid. Furthermore, such compounds can be incorporated within delivery forms for human ingestion. As such, these compounds accord an excellent manner of potentially reducing generation of certain cancers attributable to the presence of naturally occurring autotaxin within the human body. Methods of inactivating autotaxin to certain degrees therewith such compounds are encompassed within invention as well.

BACKGROUND OF THE PRIOR ART

Autotaxin, also known as ATX, ENPP2 or NPP2, short for Ectonucleotide pyrophosphatase phosphodiesterase 2, is an enzyme secreted within the human body. This molecule has been known for generating (LPA) through conversion of lysophosphatidyl-choline (LPC) thereto via lysophospholipase D activity (the removal of choline from the base compound generates LPA). LPA has been realized to contribute to tumor cell growth, unfortunately, as the reactivity within the human body of LPA within certain tissues has resulted, in certain studies, in cancerous growths when present at certain levels. In this manner, then, it has been theorized that the greater the incidence of autotaxin activity within the human body, the greater the possibility of LPA generation. A reduction in the catalytic capabilities of autotaxin to convert the LPC molecule to LPA would theoretically permit an ultimate reduction in possibility of unwanted cell proliferation through reduced LPA presence within a subject's body.

The mechanism of autotaxin in terms of enzymatic activity and catalysis to form LPA resides in its phosphodiesterase capability. LPA can be generated from the cleavage of the phosphodiester bonds of LPC, through the function of a phospholipase enzyme (note Formula I).

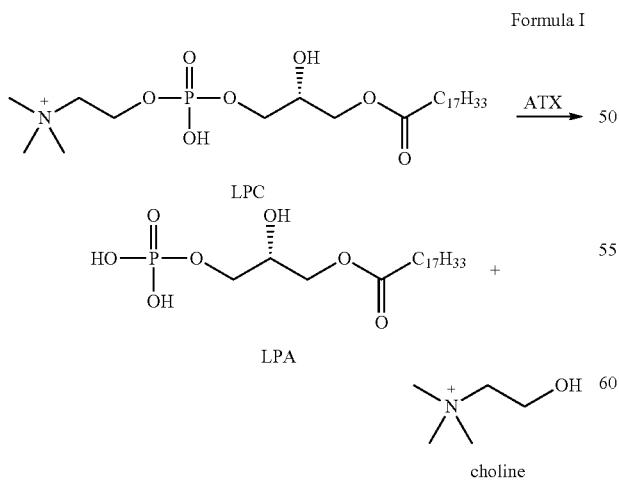

Formula I

In extracellular fluids, this enzymatic catalysis of LPC removes the choline group, leaving LPA, which has a tendency to stimulate cell growth and proliferation as well as chemotaxis. From this, it appears that the motility of tumor cells is increased as well, resulting in properties and gene expression within certain carcinomas (such as, for instance, breast cancer cells), causing further processing into a form that is bioactive and potentially dangerous. Metastasis and oncogenesis of cancer cells appear to occur as well with elevated levels of LPA present within a targeted region. Increased ATX expression has been identified in renal carcinoma, metastatic breast cancer, thyroid carcinoma, Hodgkin lymphoma, and invasive glioblastoma multiforme, as well as other diseases, including multiple sclerosis, obesity, diabetes, Alzheimer's diseases, and chronic pain.

It has thus been determined that the ability to prevent, or at least reduce, the amount of LPA within the human body holds great promise at, likewise, reducing, if not preventing, the onset of certain diseases, most prominently, certain cancers. It has been theorized, as noted above, that autotaxin modifications may prevent the undesirable conversion from LPC to LPA; the ability to actually accomplish such a result has been elusive, however, at least to the degree necessary for effective broad-scale utilization of such a method. Any modification thereof must exhibit an ability to drastically reduce the activity of autotaxin while also, preferably exhibiting oral bioavailability as well.

Autotaxin (ATX, NPP2) was originally identified as an autocrine motility factor in the conditioned media of A2058 melanoma cells. Subsequently, ATX was shown to be, as discussed above, the lysophospholipase D enzyme responsible for synthesis of the bioactive lipid lysophosphatidic acid (LPA) in vivo. Specific, potent inhibitors of ATX are therefore desirable as novel therapeutic leads.

Examples of metal chelators, lipid analogs and non-lipid, small molecules have all been identified as autotaxin inhibitors. Metal chelators such as EDTA, phenanthroline, and L-histidine have been shown to inhibit ATX activity, presumably via interactions with active site divalent metal ions required for function. Lipid analogs represent the largest group of reported ATX inhibitors (see FIG. 1 for structures). LPA and the related bioactive lipid sphingosine 1-phosphate (S1P) were previously shown to function as feedback inhibitors of ATX. This discovery led to the analysis of several LPA and S1P analogs as ATX inhibitors. Reported LPA analogs include fatty alcohol phosphates, Darmstoff analogs, cyclic phosphatidic acid analogs, and phosphonates (VPC8a202, S32826, and JGW-8). One reported S1P analog, FTY720-phosphate, has also been examined as an ATX inhibitor (structures of these types of previous ATX inhibiting compounds are provided below).

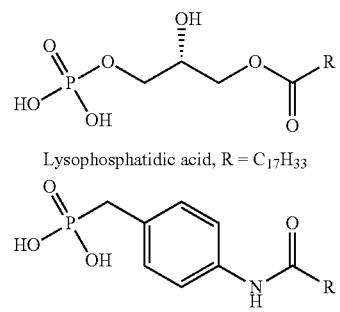

Lysophosphatidic acid, $R = C_{17}H_{33}$

[4-(tetradecanoylamino)benzyl]phosphonic acid (S32826), $R = C_{13}H_{27}$

-continued

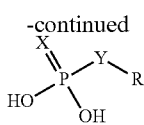

Fatty alkyl phosphonate, X = O, Y = CH$_2$, R = C$_{13}$H$_{27}$
Fatty alkyl thiophosphate, X = S, Y = O, R = C$_{18}$H$_{35}$

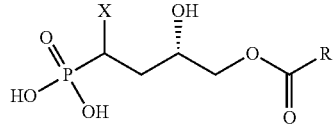

Alpha-substituted phosphonic acids (JGW-8),
R = C$_{17}$H$_{33}$ or C$_{15}$H$_{31}$, X = H, Cl, Br, or OH

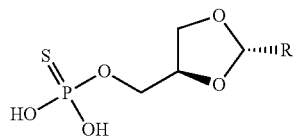

Darmstoff analog, R = C$_{17}$H$_{33}$

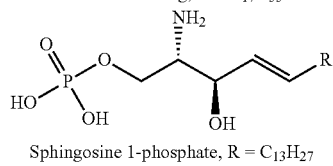

Sphingosine 1-phosphate, R = C$_{13}$H$_{27}$

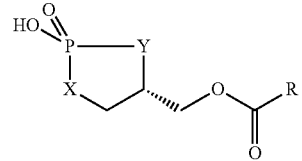

2-Carba cyclic phosphatidic acid, X = O, Y = CH$_2$
3-Carba cyclic phosphatidic acid, X = CH$_2$, Y = O

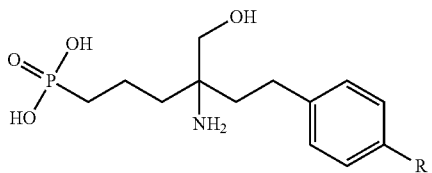

FTY720-phosphate, R = C$_8$H$_{17}$

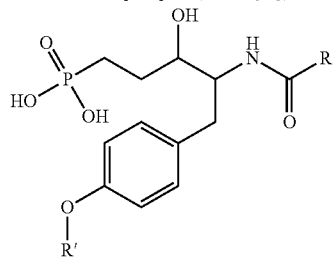

Phosphonates (VPC8a202), R = C$_{15}$H$_{31}$,
R' = aromatic, heteroaromatic, cyclohexyl While many of these lipid analogs are potent ATX inhibitors, they lack many characteristics seen in 90% of orally bioavailable drugs, and collectively they lack significant structural diversity.

Finally, the third category of reported ATX inhibitors consists of non-lipid, small molecules that collectively extend structural diversity and in general possess physicochemical characteristics more closely related to orally bioavailable drugs. The most efficacious structures previously identified are shown in group Figure A, below. H2L 7905958 (1) was the most efficacious compound from that initial single concentration screen (at 10 µM compound 1 fully inhibited ATX-catalyzed hydrolysis of 1 µM FS-3). Recently, additional small-molecule inhibitors of ATX (group Figures B and C) were identified as potential as metastasis blockers as well. One compound, NSC 48300, in group Figure C, showed essentially 100% inhibition of melanoma metastasis at micromolar concentrations. Although this compound, and the group of compounds similar thereto, exhibited acceptable, if not effective autotaxin inhibition, it is not clear if such compounds are selective to ATX (NPP2).

A

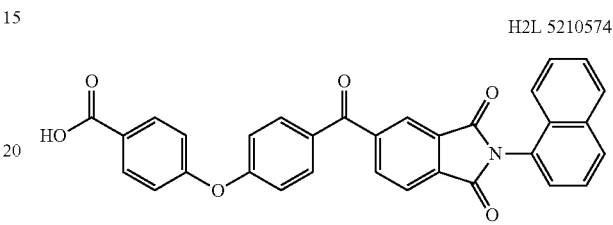

H2L 5210574

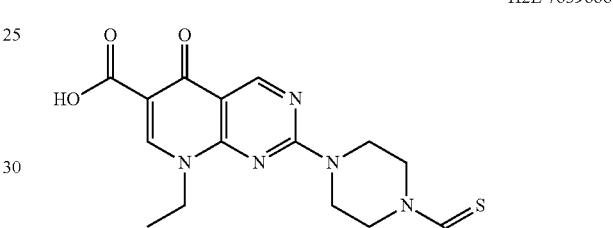

H2L 7839888

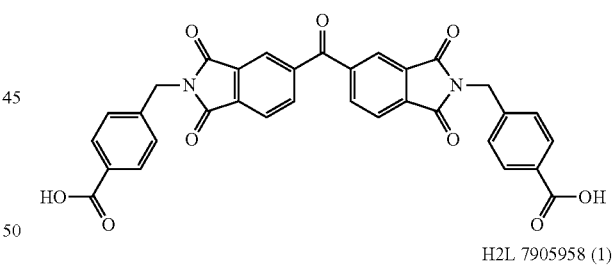

H2L 5761473

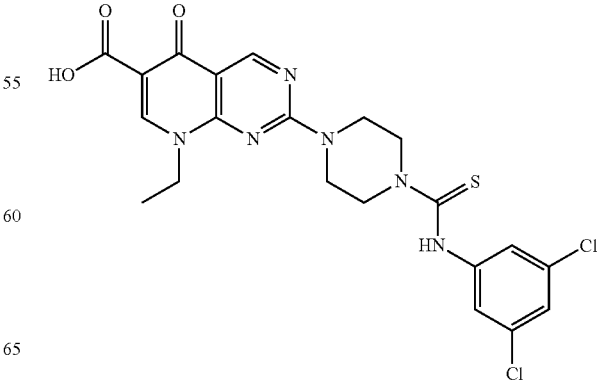

H2L 7905958 (1)

-continued

H2L 5564949
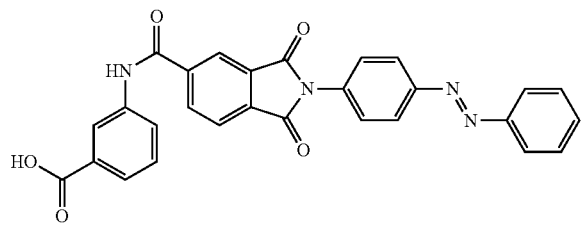

H2L 7921385
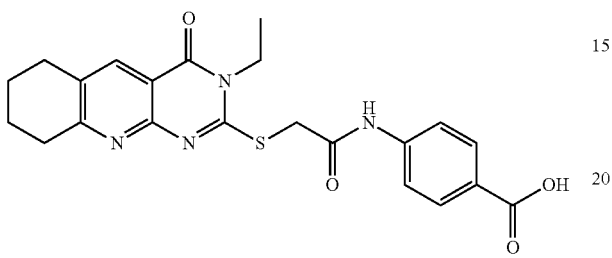

B
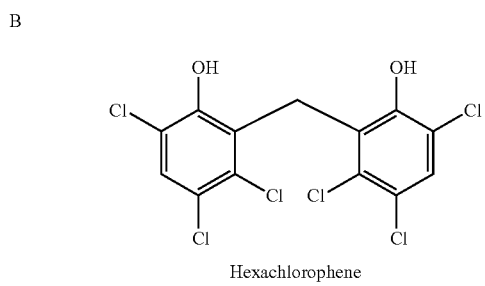
Hexachlorophene

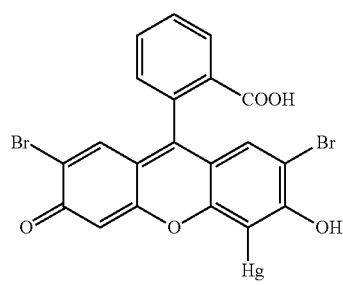
Merbromin

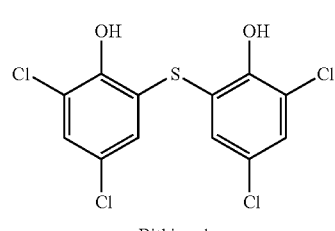
Bithionol

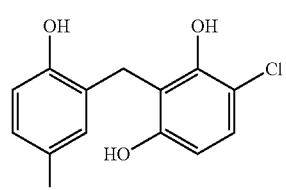
2,2'-methylenebis(4-chlorophenol)

-continued
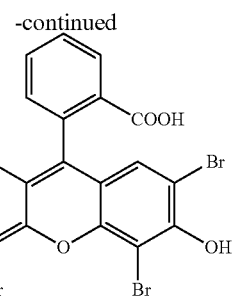
Eosin Y

RJC 03297
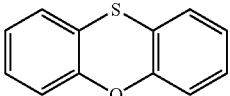

C

NSC48300
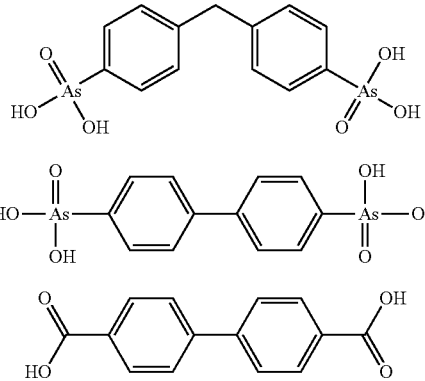

NSC13792
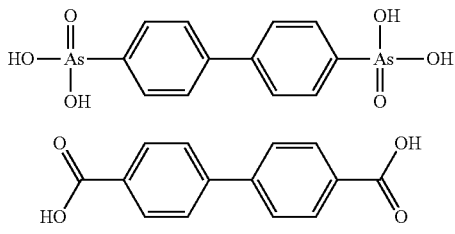

NSC60016
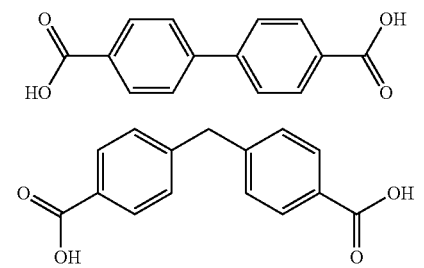

NSC86629
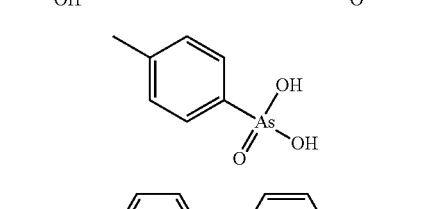

NSC10881
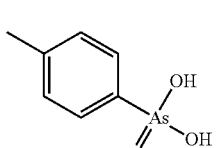

NSC78785
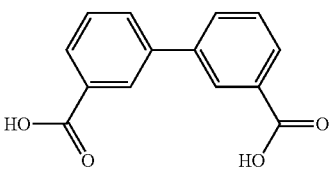

Furthermore, the previous ATX inhibiting compounds all exhibited certain drawbacks in largescale potential utilization. For instance, past work at ATX inhibition has included, as noted above, L-histidine. Unfortunately, millimolar concentrations were required for any efficacy, and, more importantly, zinc sulfate reversal of this effect (in submillimolar concentrations) suggested an inhibition mechanism involving interaction with the two native active site metal ions thereof. Other potential ATX inhibitors have included the products of ATX-catalyzed hydrolysis of LPC and sphingosyl phosphorylcholine (SPC), LPA, and S1P, respectively. Inhibition of ATX by LPA and S1P suggests that product feedback inhibition may contribute to regulation of ATX function in vivo. Additional reported ATX inhibitors share several common structural features, including a phosphate, thiophosphate, or phosphonate headgroup attached either with or without a linker to an alkyl chain, which can vary in overall length and can be either saturated or unsaturated. However, these compounds lack substantial structural diversity for possible additive or synergistic effect at improving ATX reduction. For oral ingestion purposes, as well, it is of great importance to identify novel non-lipid structural classes capable of inhibiting ATX that are structurally dissimilar from those currently used for this purpose.

It is believed, without relying upon any specific scientific basis, that the lack of diversity in reported ATX inhibitors, as noted above, is due, in part, to the lack of a characterized three-dimensional structure of the enzyme itself. The ATX sequence of over 860 amino acids is divided into several domains, including a central catalytic domain composed of about 400 amino acids. ATX is a member of the nucleotide pyrophosphatase/phosphodiesterase (NPP) family, as well as the alkaline phosphatase superfamily. Crystallographic structures of several alkaline phosphatase superfamily members have been available for decades. These crystal structures show remarkable structural conservation in a small core surrounding the catalytic site, but unfortunately show completely different structural characteristics outside this conserved core. Sequence homology of the alkaline phosphatases with ATX does not exceed 14% and is therefore insufficient for generation of a high quality homology model in any region outside the approximately 100 amino acid structurally conserved core. The recent report of a crystal structure of a bacterial NPP enzyme with 30% identity to the ATX catalytic core domain enabled the development of a structural model of the ATX catalytic domain that may prove useful in structure-based drug design. Although a significant improvement, such a homology model must be applied cautiously as involvement of the c-terminal nuclease-like domain in substrate recognition has been suggested from studies of NPP family domain-swapping chimeras. In any event, these previously reported ATX inhibitors are analogs of LPA, a phospholipid, and are more hydrophobic than is typical of orally bioavailable drugs, thereby creating problems in that area.

As such, there exists a definitive lack in providing effective ATX inhibition (or inactivation) within the current knowledge base in this area, particularly as it concerns compounds that not only exhibit ATX inhibition, but do so selectively for NPP2 alone, as compared with other NPP-type compounds (NPP6 and NPP7, for instance). The determination of proper selective NPP2 inhibiting compounds can thus aid in not only further optimization of autotaxin treatment agents, but also an understanding of the actual amino acid structures outside of the ATX conservative core. As such, although some compounds may promote ATX inhibition as they currently exist, some others with homologous structures (at least to a certain degree) to such effective ATX reduction agents may serve as intermediate compounds for further reaction and/or modification for such an optimization process.

As noted above, previous attempts at such treatments have provided developments of certain classes of compounds that exhibit certain desired results with ATX inhibition. However, the generation of classes that effectively provide increased overall ATX inhibition characteristics has been lacking in the pharmaceutical industry. The present invention provides not only improved ATX inhibiting compounds, but possible intermediates as launching pads into further improvement possibilities within this area as well.

ADVANTAGES AND BRIEF DESCRIPTION OF THE INVENTION

It is thus an advantage of the present invention to provide reliable and highly effective autotaxin inactivators for the purpose of reducing the conversion of LPC to LPA through the utilization of a readily available and easily produced compound (or compounds). Another advantage is the ability for treatment with such compounds for cancer prevention treatment regimens. Yet another advantage is the potential capability of providing combinations of different compounds that are similar in foundational structure that may exhibit a synergistic effect for further improved ATX inhibition. Still another advantage is the ability to determine effective autotaxin inhibitors through the utilization of a base identified compound via intermediate compounds made therefrom and exhibiting acceptable ATX inhibition properties, and building prospective compounds through pendant group addition through different methods (i.e., computational screening and synthetic medicinal chemistry).

Accordingly, this invention encompasses a method for reducing autotaxin activity to modify LPC to LPA, said method involving the reaction of autotaxin with at least one pipemidic acid derivative compound. In greater detail, such a treatment method would involve a reaction product of pipemidic acid and a phenylthiourea compound. More specifically, the reaction product would exhibit, preferably, though not necessarily, at least one pendant group on the ring of the phenylthiourea reactant in the meta-position to the thiourea linking group to the pipemidic acid constituent. The following figure provides a representative reaction in this manner, wherein $R_1$-$R_5$ may be selected individually from the group consisting of hydrogen, halogen, $C_1$-$C_{18}$ alkyl, $C_1$-$C_{18}$ alkoxy, $C_1$-$C_{18}$ alkenyl, $C_1$-$C_{18}$ carboxyl, $C_1$-$C_{18}$ carboxyalkyl, $C_1$-$C_{18}$ alkoxy, $C_1$-$C_{18}$ halogen-substituted alkyl, any two of such groups forms a cycloalkyl ring, any two of such groups forms an heterocyclic ring (such as including a nitrogen atom therein), with, at least one group being something other than hydrogen (and others as presented below on page 14). As noted above, preferably $R_1$, $R_3$, and $R_5$ are hydrogen, and $R_2$ and $R_4$ being any other group as noted. Most preferably only one of $R_2$ and $R_4$ is any such group other than hydrogen as well, and still more preferably wherein such a group is a halogen or a trihaloalkyl group:

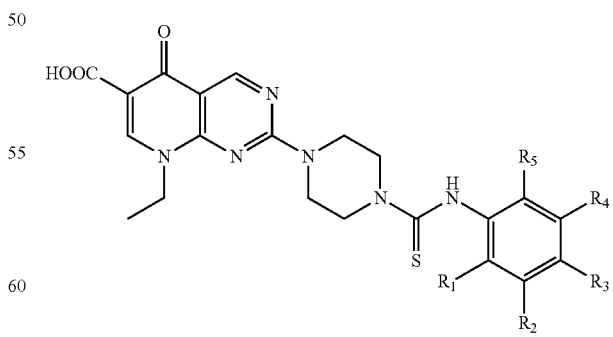

This inventive method thus concerns the treatment, via any available manner, such as intravenous, oral ingestion, and the like, of a mammalian subject to reduce autotaxin availability therein. Such an inventive method may also encompass the broad treatment of the same subject for a number of different maladies associated with autotaxin presence and activity within the subject's body (such as to treat obesity, atherosclerosis, and the like, as noted herein), rather than simply for cancer treatments alone. Additionally, the specific compounds that exhibit greater than 50% response at a single 10 μM dose and/or a $K_i$ of less than 2 μM for ATX inhibition are within the scope of this invention. Furthermore, even if the compounds that fall within the scope of the reaction product noted above do not exhibit such a threshold improvement in ATX inhibition, such compounds are still within the scope of this invention for the purpose of providing, as noted previously, intermediates for further modification and/or reaction to optimize such ATX inhibition results.

BRIEF DESCRIPTION OF THE DRAWINGS

FIG. 1 is a graphical representation of the autotaxin inhibition capability of lead compound A, as depicted below.

FIG. 2 is a graphical representation of the reactivity of lead compound A, as depicted below, in terms of Ki measurements.

DETAILED DESCRIPTION OF THE INVENTION

Figure 3:
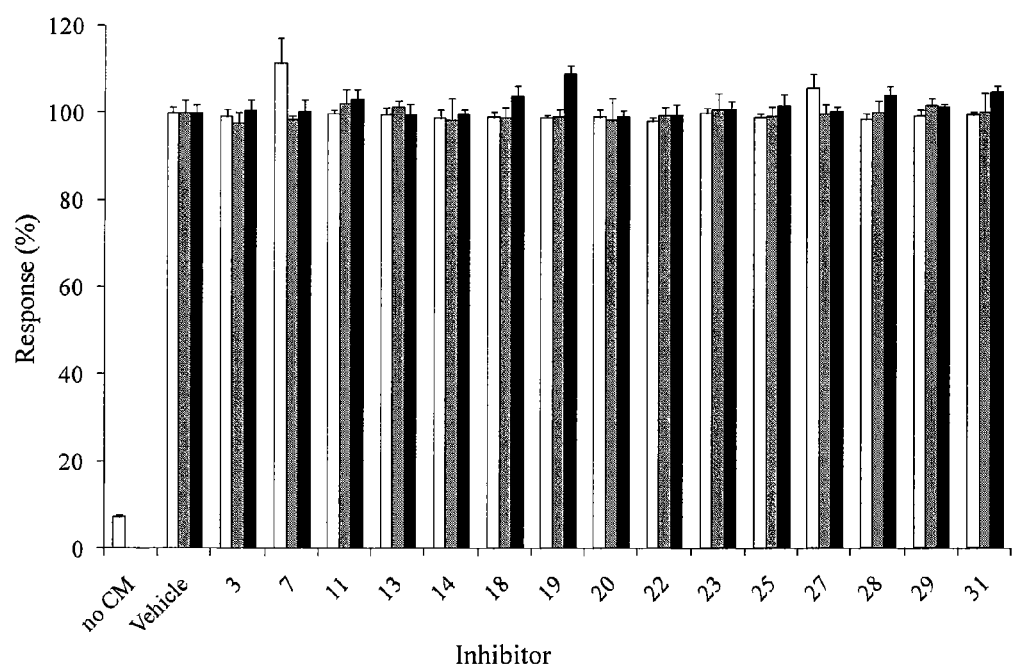
FIG. 3 is a histogram representation of autotaxin inhibition of representative inventive compounds.

Pipemidic acid itself has been used in the past as an antibacterial compound (quinolone-type antibiotics have been widely used for nearly a century, in fact). Derivatives of such a base compound have been developed as improved antibiotics as well through the years. However, such compounds have involved the modification of the actual pipemidic acid backbone (such as replacing an aza group from an heterocyclic constituent with a methyltluoro substiluent, or replacing the N-cthyl group with a N-cyclopropyl moiety, as examples) rather than reacting the pipemidic acid with an additive group and retaining the pipemidic acid backbone in total (save for the reactive hydrogen attached to the heterocyclic nitrogen). As such, although antibacterial effects may be possible with the specific compounds of this invention, primarily such compounds exhibit the target efficacy in reducing autotaxin reactivity for the conversion of LPC to LPA. The retention of the pipemidic acid backbone at this point thus eschews any relation to the antibiotic compounds of the past; a reactant product of pipemidic acid with another additive compound (such as preferably a phenylthiourea of various substitutions) is of a necessity.

The inventive compounds were in essence developed through the realization that a first small molecule ATX inhibitor, noted below as compound A exhibited high efficacy as an autotaxin inhibitor. As noted, such a compound exhibited effective response to autotaxin activity (Graph B) (FIG. 1) as well as $K_i$ at micromolar concentrations (Graph C) (FIG. 2):

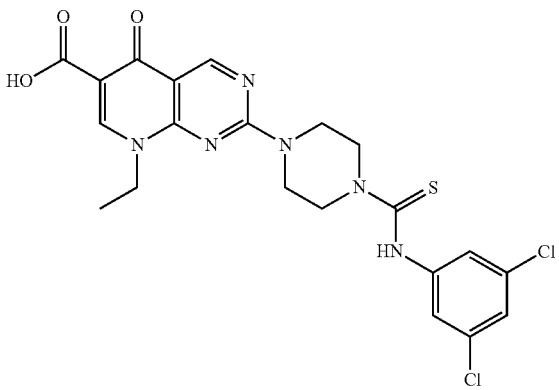

A

As is evident, this lead compound A (at 10 μM concentration) completely blocked ATX-mediated hydrolysis of the synthetic FRET reagent FS-3 (1 μM), a highly surprising result. From this realization, it was then determined that this initial compound inhibited ATX via a mixed-mode mechanism with an $IC_{50}$ of 1.6±0.4 μM and $K_i$ of 1.6 μM. Such a low micromolar inhibitor lead compound then permitted further research into potential diversification strategies to generate structure activity relationship (SAR) data for the possible identification of more potent analog compounds. It was realized, as provided in greater detail below, that the derivatization of pipemidic acid with isothiocyanate reactants was a highly effective route to a range of analogs of compound A, above bearing various substituents on the phenylthiourea motif. As provided below, an array of compounds were created with the base compound being structure A, with the different final compounds tested for ATX inhibition, etc., being those with the specific R groups as presented. The actual production methods for these compounds are presented in greater detail below.

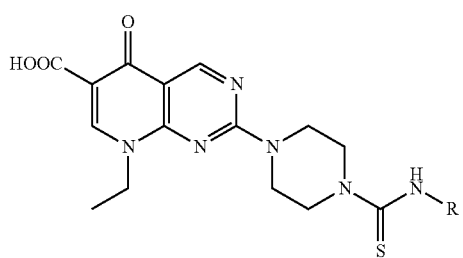

A

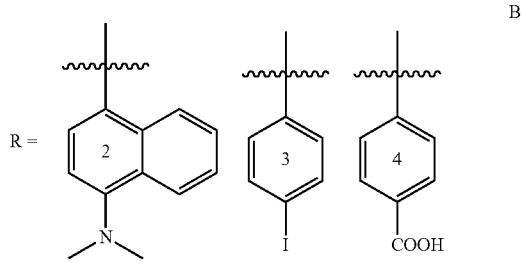

B

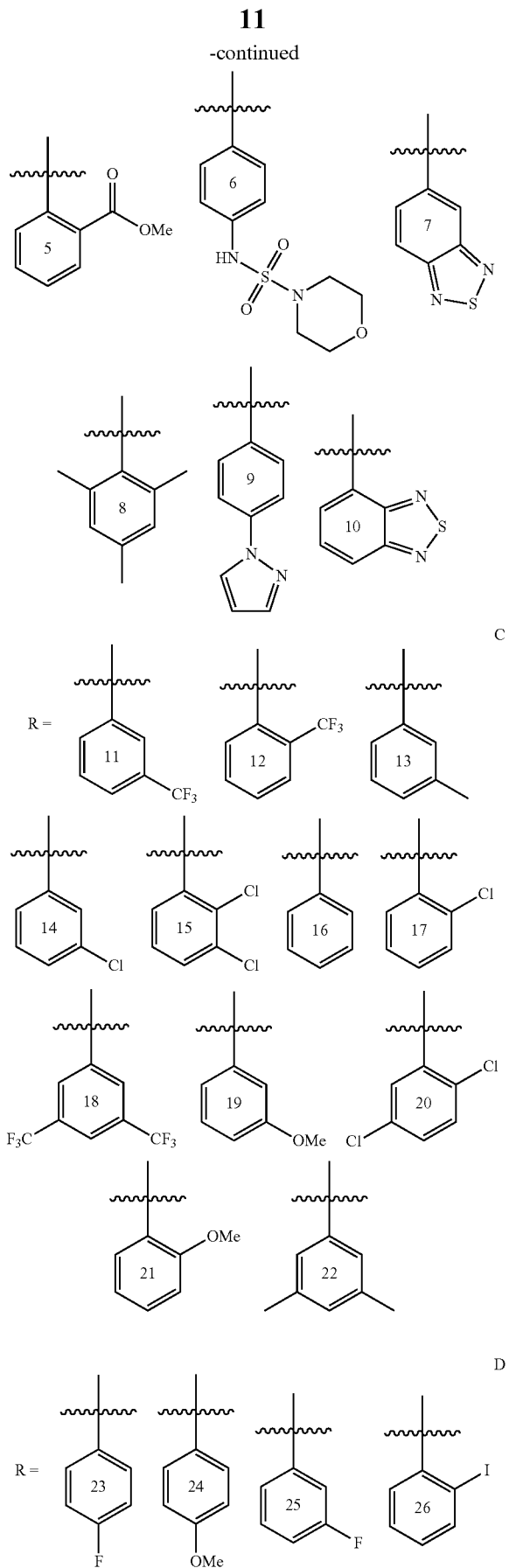
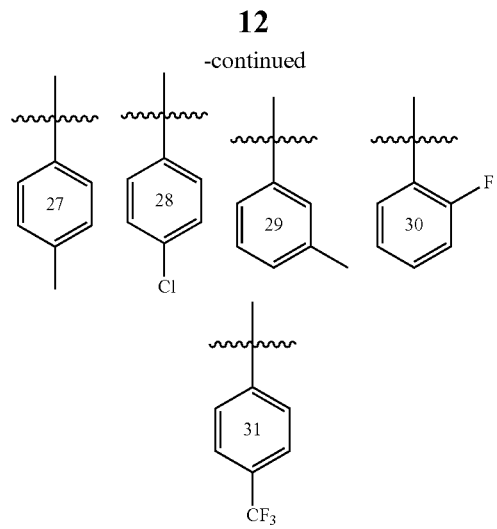

Previously published research defines inhibition mechanisms for a relatively small proportion of the known inhibitors. Inhibitors with reported mechanism of inhibition include L-histidine, LPA and S1P, FTY720-phosphate, and non-lipid small molecules. L-histidine demonstrates non-competitive inhibition. LPA and S1P demonstrated mixed-mode inhibition with LPA having a $K_i$ of ~0.1 µM, and it was reported that FTY720-phosphate inhibited ATX in the low millimolar range by a competitive mechanism with a $K_i$ of 0.2 µM. As well, it has been disclosed that certain non-lipid, small molecules, such as NSC 48300 (as provided structurally on page 6, above) demonstrated potency in nanomolar concentrations as competitive ATX inhibitors. Within the series of analogs provided above (B, C, and D, based on backbone compound A), unexpectedly it was found that certain members of these series exhibited effective competitive, uncompetitive and mixed mode ATX inhibition mechanisms. Both competitive and mixed mode inhibitors were able to achieve 100% inhibition at saturation, due to their ability to bind to the enzyme to form an enzyme-inhibitor complex. In contrast, the uncompetitive inhibitors, at saturating concentrations, could not completely inhibit hydrolysis, as they binded only to the enzyme-substrate complex. These differences clearly suggest that uncompetitive inhibitors fail to interact with the same binding pocket, thereby providing a basis for further investigation with the phenylthiourea reactants as intermediates for further reactions and, possibly more importantly, permitting a more in-depth ability to determine the actual structure of ATX itself for future computer, etc., modeling approaches. Future computational tools will therefore require experimental identification of inhibition mechanisms, which will allow for the development of distinct models for compounds with a shared inhibition mechanism.

Of additional particular interest in the ATX inhibition field is the potential for developing a compounds that exhibits specificity for ATX alone. In actuality, it appears that inhibitor specificity in the NPP family has previously not been examined. Three members of the NPP enzyme family, NPP2 (ATX), NPP6 and NPP7, share the ability to hydrolyze lysophospholipids, and therefore might be expected to have some overlap in their recognition of inhibitors. As autotaxin is the primary source for LPC conversion to the targeted LPA culprit, the ability to concentrate the effectiveness of an ATX inhibitor on that structure alone (without the appreciable potential for wasted amounts of inhibitor being used up in inhibiting other NPP-type enzymes) is a significant, albeit, as noted, unexamined possibility. The inventive pipemidic acid derivative compounds unexpectedly exhibit such a phenomenon of selectivity for ATX among the NPP isoforms with demonstrated preference for phospholipid substrates.

It is preferable that such compositions be orally ingestable, but they may, as noted above, be provided for intravenous introduction as well.

In terms of the form such compositions may take, any orally ingestable form is possible. This list includes, without limitation, liquids, liquid capsules, tablets, coated tablets, minitablets, capsules with individual beads, and the like. If in coated tablet form, such compositions may be of sustained release type, and may include a water insoluble but permeable film coating surrounding a core tablet and a particulate, water-soluble, pore-forming material dispersed within the film coating. Such a system thus provides an osmotic gradient and channel forming system. Typical coatings have included carnauba wax, cysteine hydrochloride, hydroxypropyl methylcellulose, magnesium stearate, microcrystalline cellulose, polyethylene glycol and titanium dioxide. Other therapeutic agents may be included with these anticancer (autotaxin inhibiting) agents as well, as long as neither interferes with the effectiveness of the other in the user's body.

DETAILED DESCRIPTION OF THE PREFERRED EMBODIMENTS

The specific compounds below, as well as the following exemplified methods of producing using such compounds are non-limiting in nature and are thus indicative of the preferred embodiments of this invention.
Pipemidic Acid Derivative Production The general procedure for the synthesis of such prospective ATX inhibitors was as follows (and more specifically presented within the Examples below): To a solution of pipemidic acid in N,N-dimethylformamide (1 mL) was added the corresponding substituted phenyl isothiocyanate. In some cases, triethylamine was added to speed the reaction, while in others, the addition of this base led to the formation of byproducts, and was thus avoided. The mixture was then allowed to stir at room temperature under nitrogen overnight. The solvent was then removed in vacuo and the residue was extracted twice with methylene chloride from aqueous saturated ammonium chloride. The organic layers were combined, dried with magnesium sulfate, filtered and concentrated. The resulting crude product was then purified by flash chromatography on silica gel eluting with methanol in methylene chloride (0-20%) to yield the corresponding thiourea products. Compound purity was evaluated by HPLC and products were determined to be ≧95% purity.

Example 1

Lead Compound A from above.

Example 2

2-(4-{[(4-dimethylaminonapthylphenyl)amino]carbonothioyl}-1-piperazinyl)-8-ethyl-5-oxo-5,8-dihydropyrido[2,3-d]pyrimidine-6-carboxylic acid (2)

Pipemidic acid (25 mg, 0.0824 mmol), 4-dimethylamino-1-napthylisothiocyanate (18.8 mg, 0.0824 mmol) and triethylamine (23 μL, 0.165 mmol) were used. Purification on silica yielded compound 2 in Table 1, below (23 mg, 53%). $^1$H NMR (300 MHz, CDCl$_3$) δ 9.29 (s, 1H), 8.63 (s, 1H), 8.32-8.24 (m, 1H), 8.02-7.93 (m, 1H), 7.62-7.46 (m, 3H), 7.02 (d, J=7.95 Hz, 1H), 4.29 (q, J=6.90 Hz, 2H), 4.16-3.85 (m, 8H), 2.90 (s, 6H), 1.45 (t, J=7.08 Hz, 3H) ppm.

Example 3

2-(4-{[(4-iodophenyl)amino]carbonothioyl}-1-piperazinyl)-8-ethyl-5-oxo-5,8-dihydropyrido[2,3-d]pyrimidine-6-carboxylic acid (3)

Pipemidic acid (25 mg, 0.0824 mmol), 4-iodophenyl isothiocyanate (21.5 mg, 0.0824 mmol) and triethylamine (23 μL, 0.165 mmol) were used. Purification on silica yielded compound 3 in Table 1, below (36 mg, 77%). $^1$H NMR (300 MHz, CDCl$_3$) δ 9.32 (s, 1H), 8.66 (s, 1H), 7.66 (d, J=6.94 Hz, 1H), 7.37 (s, 1H), 7.27 (s, 1H), 7.00 (d, J=7.44 Hz, 1H), 4.33 (q, J=6.90 Hz, 2H), 4.21-3.99 (m, 8H), 1.49 (t, J=7.14 Hz, 3H) ppm.

Example 4

2-(4-{[(4-carboxylphenyl)amino]carbonothioyl}-1-piperazinyl)-8-ethyl-5-oxo-5,8-dihydropyrido[2,3-d]pyrimidine-6-carboxylic acid (4)

Pipemidic acid (25 mg, 0.0824 mmol), 4-isothiocyanatobenzoic acid (14.8 mg, 0.0824 mmol) and triethylamine (23 μL, 0.165 mmol) were used. Purification on silica yielded compound 4 in Table 1, below (23 mg, 58%). $^1$H NMR (300 MHz, DMSO) δ 9.71 (s, 1H), 9.24 (s, 1H), 8.98 (s, 1H), 7.87 (d, J=8.53 Hz, 2H), 7.49 (d, J=8.43 Hz, 2H), 4.45-4.39 (m, 2H), 4.10-4.03 (m, 8H), 1.38 (t, J=6.94 Hz, 3H) ppm.

Example 5

2-(4-{[(2-methylesterphenyl)amino]carbonothioyl}-1-piperazinyl)-8-ethyl-5-oxo-5,8-dihydropyrido[2,3-d]pyrimidine-6-carboxylic acid (5)

Pipemidic acid (25 mg, 0.0824 mmol), methyl 2-isothiocyanatobenzoate (16 mg, 0.0824 mmol) and triethylamine (23 μL, 0.165 mmol) were used. Purification on silica yielded compound 5 in Table 1, below (24 mg, 59%). $^1$H NMR (300 MHz, CDCl$_3$) δ 11.14 (s, 1H), 9.35 (d, J=3.14 Hz, 1H), 8.77 (d, J=7.80 Hz, 1H), 8.69 (d, J=2.99 Hz, 1H), 8.01 (d, J=6.95 Hz, 1H), 7.55 (t, J=7.72 Hz, 1H), 7.12 (t, J=7.99 Hz, 1H), 4.38-4.12 (m, 10H), 3.92 (s, 3H), 1.51 (m, 3H) ppm.

Example 6

2-(4-{[(4-morpholinosulfonylphenyl)amino]carbonothioyl}-1-piperazinyl)-8-ethyl-5-oxo-5,8-dihydropyrido[2,3-d]pyrimidine-6-carboxylic acid (6)

Pipemidic acid (14.2 mg, 0.0468 mmol), 4-(morpholinosulfonyl)phenyl isothiocyanate (14 mg, 0.0468 mmol) and triethylamine (13 μL, 0.0935 mmol) were used. Purification on silica yielded 6 (24 mg, 85%). $^1$H NMR (300 MHz, CDCl$_3$) δ 9.28 (s, 1H), 8.65 (s, 1H), 8.09 (s, 1H), 7.64 (d, J=8.71 Hz, 2H), 7.51 (d, J=8.61 Hz, 2H), 4.43-4.01 (m, 10H), 3.80-3.70 (m, 4H), 3.04-2.98 (m, 4H), 1.49 (t, J=7.17 Hz, 3H) ppm.

Example 7

2-(4-{[(3-benzothiadiazolphenyl)amino]carbonothioyl}-1-piperazinyl)-8-ethyl-5-oxo-5,8-dihydropyrido[2,3-d]pyrimidine-6-carboxylic acid (7)

Pipemidic acid (25 mg, 0.0824 mmol), 2,1,3-benzothiadiazol-5-yl isothiocyanate (15.8 mg, 0.0824 mmol) and triethylamine (23 μL, 0.165 mmol) were used. Purification on silica yielded compound 7 in Table 1, below (24 mg, 58%). ¹H NMR (300 MHz, DMSO) δ 9.26 (s, 1H), 8.98 (s, 1H), 7.98-7.82 (m, 3H), 4.51-4.33 (m, 2H), 4.24-3.99 (m, 8H), 1.42-1.32 (m, 3H) ppm.

Example 8

2-(4-{[(2,4,6-mesitylphenyl)amino]carbonothioyl}-1-piperazinyl)-8-ethyl-5-oxo-5,8-dihydropyrido[2,3-d]pyrimidine-6-carboxylic acid (8)

Pipemidic acid (25 mg, 0.0824 mmol), mesityl isothiocyanate (14.6 mg, 0.0824 mmol) and triethylamine (23 μL, 0.165 mmol) were used. Purification on silica yielded compound 8 in Table 1, below (36.6 mg, 92%). ¹H NMR (300 MHz, CDCl₃) δ 9.32 (s, 1H), 8.64 (s, 1H), 7.05 (s, 1H), 6.92 (s, 2H), 4.41-3.93 (m, 10H), 2.28 (s, 3H), 2.23 (s, 6H), 1.50 (t, J=6.96 Hz, 3H) ppm.

Example 9

2-(4-{[(4-pyrazolephenyl)amino]carbonothioyl}-1-piperazinyl)-8-ethyl-5-oxo-5,8-dihydropyrido[2,3-d]pyrimidine-6-carboxylic acid (9)

Pipemidic acid (27 mg, 0.0894 mmol) and 4-(1H-pyrazol-1-yl)phenyl isothiocyanate (15 mg, 0.0745 mmol) were used. Purification on silica yielded compound 9 in Table 1, below (35.5 mg, 94%). ¹H NMR (250 MHz, CDCl₃) δ 9.30 (s, 1H), 8.69 (s, 1H), 7.91 (s, 1H), 7.72-7.56 (m, 3H), 7.46-7.30 (m, 2H), 6.46 (s, 1H), 4.36 (q, J=7.25 Hz, 2H), 4.28-3.96 (m, 8H), 1.48 (t, J=7.04 Hz, 3H) ppm.

Example 10

2-(4-{[(2-benzothiadiazolphenyl)amino]carbonothioyl}-1-piperazinyl)-8-ethyl-5-oxo-5,8-dihydropyrido[2,3-d]pyrimidine-6-carboxylic acid (10)

Pipemidic acid (25 mg, 0.0824 mmol), 2,1,3-benzothiadiazol-4-yl isothiocyanate (16 mg, 0.0824 mmol) and triethylamine (23 μL, 0.165 mmol) were used. Purification on silica yielded compound 10 in Table 1, below (10.8 mg, 26%). ¹H NMR (300 MHz, DMSO) δ 9.81 (s, 1H), 9.27 (s, 1H), 9.00 (s, 1H), 7.93 (d, J=8.40 Hz, 1H), 7.77-7.68 (m, 1H), 7.63 (d, J=7.23 Hz, 1H), 4.48-4.41 (m, 2H), 4.24-3.99 (m, 8H), 1.39 (t, J=6.52 3H) ppm.

Example 11

2-(4-{[(3-trifluoromethylphenyl)amino]carbonothioyl}-1-piperazinyl)-8-ethyl-5-oxo-5,8-dihydropyrido[2,3-d]pyrimidine-6-carboxylic acid (11)

Pipemidic acid (25 mg, 0.0824 mmol), 3-(trifluoromethyl) phenyl isothiocyanate (12.5 μL, 0.0824 mmol) and triethylamine (23 μL, 0.165 mmol) were used. Purification on silica yielded compound 11 in Table 1, below (31 mg, 75%). ¹H NMR (300 MHz, CDCl₃) δ 9.32 (s, 1H), 8.72 (s, 1H), 7.41-7.35 (m, 1H), 7.29-7.21 (m, 2H), 7.21-7.16 (m, 1H), 4.37 (q, J=7.10 Hz, 2H), 4.27-3.93 (m, 8H), 1.50 (t, J=7.04 Hz, 3H) ppm.

Example 12

2-(4-{[(2-trifluoromethylphenyl)amino]carbonothioyl}-1-piperazinyl)-8-ethyl-5-oxo-5,8-dihydropyrido[2,3-d]pyrimidine-6-carboxylic acid (12)

Pipemidic acid (48 mg, 0.159 mmol) and 2-(trifluoromethyl)phenyl isothiocyanate (20 μL, 0.132 mmol) were used. Purification on silica yielded compound 12 in Table 1, below (55 mg, 82%). ¹H NMR (300 MHz, CDCl₃) δ 9.32 (s, 1H), 8.69 (s, 1H), 7.74-7.64 (m, 1H), 7.63-7.51 (m, 2H), 7.43-7.33 (m, 1H), 4.47-3.90 (m, 10H), 1.50 (t, J=6.86 Hz, 3H) ppm.

Example 13

2-(4-{[(3-methylphenyl)amino]carbonothioyl}-1-piperazinyl)-8-ethyl-5-oxo-5,8-dihydropyrido[2,3-d]pyrimidine-6-carboxylic acid (13)

Pipemidic acid (54 mg, 0.177 mmol) and m-tolylisothiocyanate (20 μL, 0.148 mmol) were used. Purification on silica yielded compound 13 in Table 1, below (67 mg, 100%). ¹H NMR (300 MHz, CDCl₃) δ 9.32 (s, 1H), 8.68 (s, 1H), 7.34-7.32 (m, 1H), 7.05-6.94 (m, 3H), 4.33 (q, J=7.10 Hz, 2H), 4.24-3.87 (m, 8H), 2.35 (s, 3H), 1.49 (t, J=7.19 Hz, 3H) ppm.

Example 14

2-(4-{[(3-chlorophenyl)amino]carbonothioyl}-1-piperazinyl)-8-ethyl-5-oxo-5,8-dihydropyrido[2,3-d]pyrimidine-6-carboxylic acid (14)

Pipemidic acid (25 mg, 0.0824 mmol), 3-chlorophenyl isothiocyanate (11 μL, 0.0824 mmol) and triethylamine (23 μL, 0.165 mmol) were used. Purification on silica yielded compound 14 in Table 1, below (8.2 mg, 21%). ¹H NMR (300 MHz, CDCl₃) δ 9.03 (s, 1H), 8.51 (s, 1H), 7.10 (s, 1H), 7.04-6.93 (m, 2H), 6.90-6.84 (m, 1H), 4.14 (q, J=6.90 Hz, 2H), 4.00-3.74 (m, 8H), 1.23 (t, J=7.01 Hz, 3H) ppm.

Example 15

2-(4-{[(2,3-dichlorophenyl)amino]carbonothioyl}-1-piperazinyl)-8-ethyl-5-oxo-5,8-dihydropyrido[2,3-d]pyrimidine-6-carboxylic acid (15)

Pipemidic acid (51 mg, 0.168 mmol) and 2,3-dichlorophenyl isothiocyanate (20 μL, 0.141 mmol) were used. Purification on silica yielded compound 15 in table 1, below (15.5 mg, 22%). ¹H NMR (300 MHz, DMSO) δ 9.03 (s, 1H), 8.78 (s, 1H), 7.53 (d, J=7.43 Hz, 1H), 7.41-7.26 (m, 2H), 4.51-3.90 (m, 10H), 1.43-1.27 (m, 3H) ppm.

Example 16

2-(4-{[(phenyl)amino]carbonothioyl}-1-piperazinyl)-8-ethyl-5-oxo-5,8-dihydropyrido[2,3-d]pyrimidine-6-carboxylic acid phenyl (16)

Pipemidic acid (25 mg, 0.0824 mmol), phenyl isothiocyanate (9.8 μL, 0.0824 mmol) and triethylamine (23 μL, 0.165 mmol) were used. Purification on silica yielded compound 16 in Table 1, below (16 mg, 43%). ¹H NMR (300 MHz, CDCl₃) δ 9.33 (s, 1H), 8.68 (s, 1H), 7.41-7.33 (m, 3H), 7.22-7.15 (m, 2H), 4.38-4.28 (m, 2H), 4.24-3.89 (m, 8H), 1.49 (t, J=7.57 Hz, 3H) ppm.

Example 17

2-(4-{[(2-chlorophenyl)amino]carbonothioyl}-1-piperazinyl)-8-ethyl-5-oxo-5,8-dihydropyrido[2,3-d]pyrimidine-6-carboxylic acid (17)

Pipemidic acid (56 mg, 0.184 mmol) and 2-chlorophenylisothiocyanate (20 µL, 0.153 mmol) were used. Purification on silica yielded compound 17 in Table 1, below (72 mg, 99%). $^1$H NMR (300 MHz, CDCl$_3$) δ 9.34 (s, 1H), 8.68 (s, 1H), 7.75 (d, J=8.10 Hz, 1H), 7.44 (d, J=8.00 Hz, 1H), 7.37-7.27 (m, 2H), 7.15 (t, J=7.67 Hz, 1H), 4.35 (q, J=7.15 Hz, 2H), 4.29-4.01 (m, 8H), 1.50 (t, J=7.20 Hz, 3H) ppm.

Example 18

2-(4-{[(3,5-bis(trifluoromethyl)phenyl)amino]carbonothioyl}-1-piperazinyl)-8-ethyl-5-oxo-5,8-dihydropyrido[2,3-d]pyrimidine-6-carboxylic acid (18)

Pipemidic acid (40 mg, 0.132 mmol) and 3,5-bis(trifluoromethyl)phenyl isothiocyanate (20 µL, 0.110 mmol) were used. Purification on silica yielded compound 18 in Table 1, below (61 mg, 97%). $^1$H NMR (300 MHz, CDCl$_3$) δ 9.30 (s, 1H), 8.68 (s, 1H), 8.62 (s, 1H), 7.94 (s, 2H), 7.62 (s, 1H), 4.42-4.05 (m, 10H), 1.51 (t, J=7.07 Hz, 3H) ppm.

Example 19

2-(4-{[(3-methoxyphenyl)amino]carbonothioyl}-1-piperazinyl)-8-ethyl-5-oxo-5,8-dihydropyrido[2,3-d]pyrimidine-6-carboxylic acid (19)

Pipemidic acid (25 mg, 0.0824 mmol), 3-methoxyphenyl isothiocyanate (11.6 µL, 0.0824 mmol) and triethylamine (23 µL, 0.165 mmol) were used. Purification on silica yielded compound 19 in Table 1, below (21.4 mg, 55%). $^1$H NMR (300 MHz, CDCl$_3$) δ 9.31 (s, 1H), 8.67 (s, 1H), 7.47 (s, 1H), 7.30-7.21 (m, 1H), 6.80-6.68 (m, 3H), 4.32 (q, J=6.90 Hz, 2H), 4.23-3.89 (m, 8H), 3.79 (s, 3H), 1.48 (t, J=7.16 Hz, 3H) ppm.

Example 20

2-(4-{[(2,5-dichlorophenyl)amino]carbonothioyl}-1-piperazinyl)-8-ethyl-5-oxo-5,8-dihydropyrido[2,3-d]pyrimidine-6-carboxylic acid (20)

Pipemidic acid (51 mg, 0.168 mmol) and 2,5-dichlorophenyl isothiocyanate (20 µL, 0.140 mmol) were used. Purification on silica yielded compound 20 in Table 1, below (42.7 mg, 60%). $^1$H NMR (300 MHz, CDCl$_3$) δ 9.39 (s, 1H), 9.06 (s, 1H), 7.57 (d, J=2.39 Hz, 1H), 7.42-7.36 (m, 1H), 7.20 (d, J=7.35 Hz, 1H), 4.55-4.39 (m, 2H), 4.31-4.02 (m, 8H), 1.52 (t, J=6.88 Hz, 3H) ppm.

Example 21

2-(4-{[(2-methoxyphenyl)amino]carbonothioyl}-1-piperazinyl)-8-ethyl-5-oxo-5,8-dihydropyrido[2,3-d]pyrimidine-6-carboxylic acid (21)

Pipemidic acid (53 mg, 0.175 mmol) and 2-methoxyphenyl isothiocyanate (20 µL, 0.145 mmol) were used. Purification on silica yielded compound 21 in Table 1, below (36 mg, 53%). $^1$H NMR (250 MHz, CDCl$_3$) δ 9.33 (s, 1H), 8.68 (s, 1H), 7.84 (d, J=7.30 Hz, 1H), 7.54 (s, 1H), 7.20-7.04 (m, 1H), 7.03-6.85 (m, 2H), 4.44-3.73 (m, 13H), 1.49 (t, J=6.60 Hz, 3H) ppm.

Example 22

2-(4-{[(3,5-dimethylphenyl)amino]carbonothioyl}-1-piperazinyl)-8-ethyl-5-oxo-5,8-dihydropyrido[2,3-d]pyrimidine-6-carboxylic acid (22)

Pipemidic acid (45 mg, 0.148 mmol), 3,5-dimethylphenyl isothiocyanate (24 mg, 0.148 mmol) and triethylamine (41 µL, 296 mmol) were used. Purification on silica yielded compound 22 in Table 1, below (41.6 mg, 67%). $^1$H NMR (300 MHz, CDCl$_3$) δ 9.30 (s, 1H), 8.66 (s, 1H), 7.48 (s, 1H), 6.86-6.75 (m, 3H), 4.33 (q, J=7.10 Hz, 2H), 4.22-3.91 (m, 8H), 2.30 (s, 6H), 1.48 (t, J=7.11 Hz, 3H) ppm.

Example 23

2-(4-{[(4-fluorophenyl)amino]carbonothioyl}-1-piperazinyl)-8-ethyl-5-oxo-5,8-dihydropyrido[2,3-d]pyrimidine-6-carboxylic acid (23)

Pipemidic acid (35 mg, 0.1154 mmol) and 4-fluorophenyl isothiocyanate (17.7 mg, 0.1154 mmol) were used. Purification on silica yielded compound 23 in Table 1, below (30 mg, 57%). $^1$H NMR (300 MHz, CDCl$_3$) δ 9.34 (s, 1H), 8.69 (s, 1H), 7.33 (s, 1H), 7.25-7.16 (m, 2H), 7.13-7.03 (m, 2H), 4.34 (q, J=7.00 Hz, 2H), 4.28-3.96 (m, 8H), 1.50 (t, J=7.36 Hz, 3H) ppm.

Example 24

2-(4-{[(4-methoxyphenyl)amino]carbonothioyl}-1-piperazinyl)-8-ethyl-5-oxo-5,8-dihydropyrido[2,3-d]pyrimidine-6-carboxylic acid (24)

Pipemidic acid (30 mg, 0.0989 mmol) and 4-methoxyphenyl isothiocyanate (13.7 µL, 0.0989 mmol) were used. Purification on silica yielded compound 24 in Table 1, below (37 mg, 80%). $^1$H NMR (300 MHz, CDCl$_3$) δ 9.33 (s, 1H), 8.67 (s, 1H), 7.30 (s, 1H), 7.15 (d, J=8.76 Hz, 2H), 6.90 (d, J=8.82 Hz, 2H), 4.34 (q, J=7.10 Hz, 2H), 4.25-3.92 (m, 8H), 3.81 (s, 3H), 1.49 (t, J=7.12 Hz, 3H) ppm.

Example 25

2-(4-{[(3-fluorophenyl)amino]carbonothioyl}-1-piperazinyl)-8-ethyl-5-oxo-5,8-dihydropyrido[2,3-d]pyrimidine-6-carboxylic acid (25)

Pipemidic acid (25 mg, 0.0824 mmol) and 3-fluorophenyl isothiocyanate (9.9 µL, 0.0824 mmol) were used. Purification on silica yielded compound 25 in Table 1, below (22 mg, 59%). $^1$H NMR (300 MHz, CDCl$_3$) δ 9.32 (s, 1H), 8.66 (s, 1H), 7.41 (s, 1H), 7.37-7.27 (m, 1H), 6.96 (t, J=7.39, 2H), 6.88 (t, J=7.67 Hz, 1H), 4.38-4.27 (m, 2H), 4.27-3.91 (m, 8H), 1.54-1.43 (m, 3H) ppm.

Example 26

2-(4-{[(2-iodophenyl)amino]carbonothioyl}-1-piperazinyl)-8-ethyl-5-oxo-5,8-dihydropyrido[2,3-d]pyrimidine-6-carboxylic acid (26)

Pipemidic acid (25 mg, 0.0824 mmol) and 2-iodophenyl isothiocyanate (21.5 mg, 0.0824 mmol) were used. Purification on silica yielded compound 26 in Table 1, below (35 mg, 75%). $^1$H NMR (300 MHz, CDCl$_3$) δ 9.36-9.30 (m, 1H), 8.69-8.65 (m, 1H), 7.89-7.82 (m, 1H), 7.62-7.55 (m, 1H), 7.41-7.32 (m, 1H), 7.00-6.92 (m, 1H), 4.40-4.01 (m, 10H), 1.53-1.44 (m, 3H) ppm.

Example 27

2-(4-{[(4-methylphenyl)amino]carbonothioyl}-1-piperazinyl)-8-ethyl-5-oxo-5,8-dihydropyrido[2,3-d]pyrimidine-6-carboxylic acid (27)

Pipemidic acid (89 mg, 0.293 mmol) and p-tolyl isothiocyanate (40 mg, 0.268 mmol) were used. Purification on silica yielded compound 27 in Table 1, below (82 mg, 68%). $^1$H NMR (300 MHz, CDCl$_3$) δ 9.32 (s, 1H), 8.67 (s, 1H), 7.40 (s, 1H), 7.17 (d, J=7.60 Hz, 2H), 7.09 (d, J=7.44 Hz, 2H), 4.33 (q, J=6.40 Hz, 2H), 4.23-3.91 (m, 8H), 2.34 (s, 3H), 1.49 (t, J=7.03 Hz, 3H) ppm.

Example 28

2-(4-{[(4-chlorophenyl)amino]carbonothioyl}-1-piperazinyl)-8-ethyl-5-oxo-5,8-dihydropyrido[2,3-d]pyrimidine-6-carboxylic acid (28)

Pipemidic acid (58 mg, 0.191 mmol) and 4-chlorophenyl isothiocyanate (27 mg, 0.159 mmol) were used. Purification on silica yielded compound 28 in Table 1, below (50 mg, 67%). $^1$H NMR (300 MHz, CDCl$_3$) δ 9.34 (s, 1H), 8.68 (s, 1H), 7.36-7.34 (m, 2H), 7.17 (d, J=8.70 Hz, 2H), 4.39-4.28 (m, 2H), 4.28-3.93 (m, 8H), 1.49 (t, J=6.68 Hz, 3H) ppm.

Example 29

2-(4-{[(3-iodophenyl)amino]carbonothioyl}-1-piperazinyl)-8-ethyl-5-oxo-5,8-dihydropyrido[2,3-d]pyrimidine-6-carboxylic acid (29)

Pipemidic acid (40 mg, 0.133 mmol) and 3-iodophenyl isothiocyanate (29 mg, 0.111 mmol) were used. Purification on silica yielded compound 29 in Table 1, below (57 mg, 90%). $^1$H NMR (250 MHz, CDCl$_3$) δ 9.33 (s, 1H), 8.73 (s, 1H), 7.66-7.64 (m, 1H), 7.54-7.51 (m, 1H), 7.40-7.24 (m, 1H), 7.12-7.06 (m, 1H), 4.48-4.31 (m, 2H), 4.27-3.93 (m, 8H), 1.34-1.17 (m, 3H) ppm.

Example 30

2-(4-{[(2-fluorophenyl)amino]carbonothioyl}-1-piperazinyl)-8-ethyl-5-oxo-5,8-dihydropyrido[2,3-d]pyrimidine-6-carboxylic acid (30)

Pipemidic acid (25 mg, 0.0824 mmol) and 2-fluorophenyl isothiocyanate (10 µL, 0.0824 mmol) were used. Purification on silica yielded compound 30 in Table 1, below (24 mg, 64%). $^1$H NMR (300 MHz, CDCl$_3$) δ 9.35 (s, 1H), 8.69 (s, 1H), 7.64 (t, J=7.34 Hz, 1H), 7.21-7.12 (m, 3H), 4.35 (q, J=6.90 Hz, 2H), 4.28-4.02 (m, 8H), 1.50 (t, J=7.09 Hz, 3H) ppm.

Example 31

2-(4-{[(4-trifluoromethylphenyl)amino]carbonothioyl}-1-piperazinyl)-8-ethyl-5-oxo-5,8-dihydropyrido[2,3-d]pyrimidine-6-carboxylic acid (31)

Pipemidic acid (30 mg, 0.0989 mmol) and 4-trifluoromethylphenyl isothiocyanate (16.7 mg, 0.0824 mmol) were used. Purification on silica yielded compound 31 in Table 1, below (31 mg, 77%). $^1$H NMR (300 MHz, CDCl$_3$) δ 9.34 (s, 1H), 8.69 (s, 1H), 7.65-7.57 (m, 2H), 7.51 (s, 1H), 7.37-7.31 (m, 2H), 4.34 (q, J=6.80 Hz, 2H), 4.27-3.97 (m, 8H), 1.49 (t, J=7.25, 7.25 Hz, 3H) ppm.

As noted above, this invention is directed to a novel method of treating patients with suitable ATX inhibiting compounds. Such compounds were determined through a very efficient screening procedure, and exist as lead compounds with the potential to treat metastasis, obesity, neuropathic pain, atherosclerosis and rheumatoid arthritis, at least, within a mammalian body. As described above, the autotaxin (ATX) enzyme promotes cell migration and invasion, thus inhibition of ATX is of value for prevention of metastasis and the other maladies noted previously. In addition, assays were prepared for comparative reactivity measurements with other NPP isoforms (NPP6 and NPP7) (ATX is NPP2, as noted previously). Such methods were conducted as follows:

ATX Inhibition Assay

ATX inhibition was assayed using the substrate FS-3 (Echelon Biosciences, Inc., Salt Lake City, Utah, USA). The FS-3 assay used ~10 times concentrated conditioned serum-free medium (CCM) from MDA-MB-435 cells as the source of ATX, while CCM comprised one-third of the total volume. The final volume for FS-3 was comprised of the substrate at varying concentrations and 30 µM charcoal-stripped fatty acid free BSA (Sigma Aldrich) in assay buffer (1 mM each CaCl$_2$ and MgCl$_2$, 5 mM KCl, 140 mM NaCl, 50 mM Tris pH 8.0).

All assays were performed in 96-well plates with data read at 1 minute intervals by a Synergy2 system (BioTek, Winooski, Vt.). The fluorescence produced upon the hydrolysis of FS-3 was monitored using an excitation wavelength of 485 nm and an emission wavelength of 528 nm at 37° C. (Ferguson et al., 2006). Results are shown at one hour, at which point all fluorescence and absorbance changes as a function of time were linear. All readings were normalized to vehicle control after subtraction of fluorescence in the absence of CCM. Data are shown as the mean±S.D. of at least three wells. All experiments were repeated at least twice and results are shown.

ATX Kinetics Assays

ATX kinetics assays were performed using eight different concentrations of substrate and two different concentrations of inhibitor (ChemBridge, San Diego, Calif.). The FS-3 substrate concentrations ranged from 20-0.3 µM on the plate.

The normalized fluorescence results were plotted as a function of time in order to determine initial rates. The initial rates were plotted against the substrate concentration and a rectangular hyperbolic curve was fitted to the data using the KaleidaGraph software (Synergy Software, Reading, Pa., Version 4.03). The $K_m$ and $V_{max}$ were calculated from the resulting plots. Mode of inhibition was determined from the inhibitor effect on $K_m$ and $V_{max}$ values. The dissociation constant ($K_i$) for inhibitor binding was calculated for each of the inhibitors. $K_i$ for uncompetitive inhibition was calculated using Equation 1 (Cheng and Prusoff, 1973). Equation 2 was used for competitive inhibition (Cheng and Prusoff, 1973). The average substrate $K_m$ values, 3.7+/−1.9 µM (n=22), were calculated using the individual $K_m$ values determined using rectangular hyperbolic curve fitting of plots of initial velocity versus substrate concentration from of all inhibition analyses for FS-3. For mixed mode inhibition $K_i$=IC$_{50}$ was assumed (Burlingham and Widlanski, 2003).

$$K_i = \frac{IC_{50}}{1 + (K_m/[S])} \quad (1)$$

$$K_i = \frac{IC_{50}}{1 + ([S]/K_m)} \quad (2)$$

ATX Expression Tests

MDA-MB-435 cells were cultured at 37° C. under a humidified atmosphere containing 5% $CO_2$ in Dulbecco's Modified Eagle Medium (DMEM) (MediaTech, Herndon, Va.) containing 100 U/ml penicillin, 100 µg/ml streptomycin (Hyclone, Logan, Utah), 5% fetal bovine serum (FBS) (Hyclone, Logan, Utah), and 2 mM L-glutamine (Hyclone, Logan, Utah). Upon reaching 80 to 95% confluency, the cells were washed twice with sterile phosphate buffered saline. Serum-free DMEM containing L-glutamine and antibiotics was then added to the cells. Conditioned media was collected after 36-48 hours of incubation with serum-free DMEM. The media was concentrated ~10× and buffer exchanged into Tris (50 mM, pH 7.4) containing 20% ethylene glycol using 30 kDa molecular weight cutoff filters (Millipore, Beverly, Mass.) in an Amico pressure cell (Millipore, Beverly, Mass.). Aliquots of 10× conditioned media were stored at 4° C.

Determination of NPP6 and NPP7 Inhibition

Inhibitor selectivity was assayed using p-nitrophenylphosphoryl-choline (pNPPC) (Sigma-Aldrich, St. Louis, Mo.) as substrate for NPP6 and NPP7. The final volume (60 µL) included 20 µL (CM, NPP6 or CCM, NPP7, 20 µL inhibitor (10 µM including 1% DMSO) in assay buffer, and 20 µL pNPPC (10 mM, NPP6 or 1 NPP7) in assay buffer. NPP6 assay buffer contained 500 mM NaCl, 0.05% Triton X-100, 100 mM Tris-HCl (pH 9.0), whereas NPP7 assay buffer was comprised of 50 mM Tris HCl, pH 8.5, 150 mM NaCl, and 10 mM taurocholic acid. However, unlike the published methods, EDTA was not added to the NPP7 assay buffer. All assays were performed in 96-well, half area plates (Corning Inc., Lowell, Mass.) at 37° C. with data collected at 2 minute intervals using a Synergy2 absorbance plate reader (BioTek, Winooski, Vt.). Results are shown at the one hour time point, when all absorbance changes as a function of time were linear. Readings were normalized to vehicle control after subtraction of absorbance in the absence of CM or CCM. Data are shown as the mean±S.D. of at least three wells. All experiments were repeated twice and representative results are shown.

Assays were performed with CM or CCM from HEK293 cells transiently transfected with NPP6 and 7 expression plasmids, respectively. HEK293 cells were seeded in Dulbecco's modified Eagle's medium (DMEM) containing 10% fetal bovine serum, 100 U/ml penicillin, 100 µg/ml streptomycin (Hyclone, Logan, Utah), and 2 mM L-glutamine. HEK293 cells were grown overnight at 37° C. under 5% $CO_2$ to 80% confluence. The cells were then transfected with human NPP6ex[51] or human NPP7ex expression plasmids in the pcDNA3.1(+) mammalian vector in the presence of Polyfect Transfection Reagent (Hyclone, Logan, Utah). Six hours after transfection, the culture medium was changed to serum free DMEM containing L-glutamine and cells were incubated for 48 hours. Expressed protein was collected (NPP6 and NPP7) and concentrated ~10×(NPP7) using 10 kDa molecular weight cutoff filters (Millipore, Beverly, Mass.) in an Amicon pressure cell (Millipore, Beverly, Mass.).

Test Results

Figure 5:
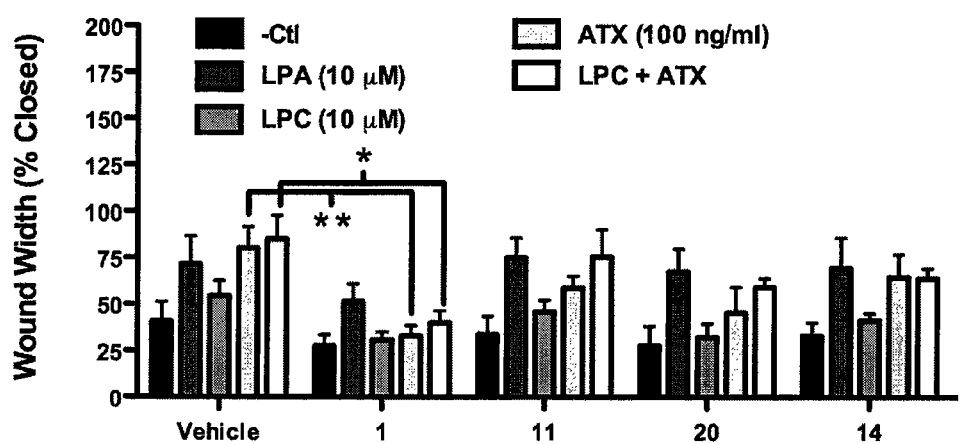
FIG. 5 is a histogram representation of cell migration characteristics related to certain representation inventive compounds.

Table 1 shows the results of SAR elaboration and optimization of lead compound H2L7905958 (1). Compounds showing improved $K_i$ values over the lead are emphasized in bold italic font. Values shown in parentheses refer to the compound numbers (FIG. 5). Errors where indicated are standard deviations of at least three independent experiments. $IC_{50}$ values lacking standard deviations are averages of two independent experiments that were less than 3% different in value.

TABLE 1

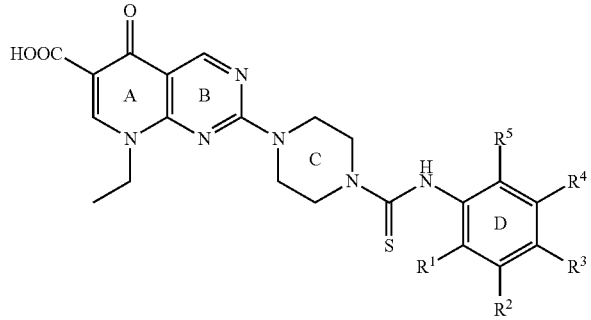

| Substitution on D ring | | % Response at 10 µM (FS-3) | $IC_{50}$ (µM) | Inhibition Mechanism | $K_i$ (µM) |
|---|---|---|---|---|---|
| LEAD-Dichloro ($R^2$, $R^4$) | (1) | 0.0 ± 4.0 | 1.6 ± 0.4 | Mixed | 1.6 |
| *Trifluoromethyl (meta-$R^2$)* | (11) | 0.3 ± 0.6 | 0.9 ± 0.3 | Competitive | 0.03 |
| Dichloro ($R^1$, $R^4$) | (20) | 5.4 ± 0.4 | 1.7 | Mixed | 1.7 |
| *Iodo (meta-$R^2$)* | (29) | 8.6 ± 0.9 | 1.6 | Uncompetitive | 1.5 |
| Chloro (meta-$R^2$) | (14) | 9.7 ± 0.9 | 2.5 ± 0.2 | Mixed | 2.5 |
| *Thiadiazole ($R^2$, $R^3$)* | (7) | 28.6 ± 2.0 | 12.1 ± 2.4 | Competitive | 0.43 |

TABLE 1-continued

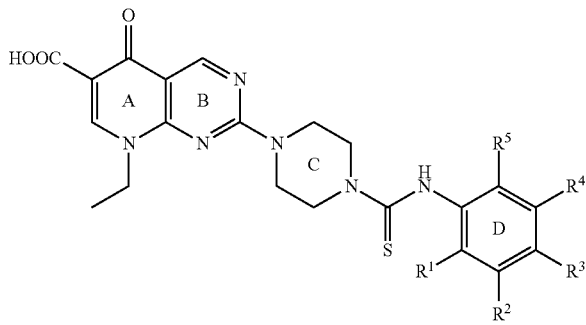

| Substitution on D ring | | % Response at 10 µM (FS-3) | IC$_{50}$ (µM) | Inhibition Mechanism | K$_i$ (µM) |
|---|---|---|---|---|---|
| Dimethyl (R$^2$, R$^4$) | (22) | 30.4 ± 1.3 | 9.0 | Mixed | 9.0 |
| Iodo (para-R$^3$) | (3) | 32.7 ± 1.3 | 5.6 ± 0.2 | Mixed | 5.6 |
| *Ditrifluoromethyl (R$^2$, R$^4$)* | (18) | 34.1 ± 3.0 | 4.4 ± 1.5 | Competitive | 0.16 |
| *Trifluoromethyl (para-R$^3$)* | (31) | 36.2 ± 0.9 | 1.5 | Uncompetitive | 1.4 |
| Fluoro (meta-R$^2$) | (25) | 40.5 ± 1.0 | 16.1 ± 4.5 | | |
| Methoxy (meta-R$^2$) | (19) | 40.9 ± 1.3 | 17.7 ± 0.3 | | |
| Methyl (meta-R$^2$) | (13) | 41.9 ± 0.8 | 13.5 ± 1.3 | Mixed | 13.5 |
| Chloro (para-R$^3$) | (28) | 42.4 ± 0.9 | 10.7 | Mixed | 10.7 |
| Fluoro (para-R$^3$) | (23) | 48.9 ± 1.1 | 17.7 | | |
| Methyl (para-R$^3$) | (27) | 49.9 ± 1.5 | 16.1 ± 4 | | |
| o-methyl ester | (5) | 51.2 ± 1.3 | | | |
| Trimethyl (R$^1$, R$^3$, R$^5$) | (8) | 53.5 ± 1.6 | | | |
| H | (16) | 56.4 ± 1.0 | | | |
| 4-dimethylaminonapthyl | (2) | 59.9 ± 1.5 | | | |
| Thiadiazole (R$^1$, R$^2$) | (10) | 63.2 ± 2.8 | | | |
| Sulfonylmorpholine (para-R$^3$) | (6) | 64.1 ± 2.8 | | | |
| Iodo (ortho-R$^1$) | (26) | 68.4 ± 1.3 | | | |
| Pyrazole (para-R$^3$) | (9) | 68.6 ± 1.1 | | | |
| Dichloro (R$^1$, R$^2$) | (15) | 72.3 ± 0.4 | | | |
| p-carboxyl | (4) | 72.7 ± 2.2 | | | |
| Fluoro (ortho-R$^1$) | (30) | 77.3 ± 1.6 | | | |
| Methoxy (para-R$^3$) | (24) | 79.7 ± 0.9 | | | |
| Chloro (ortho-R$^1$) | (17) | 83.5 ± 8.2 | | | |
| Methoxy (ortho-R$^1$) | (21) | 97.6 ± 1.8 | | | |
| Trifluoromethyl (ortho-R$^1$) | (12) | 100.8 ± 1.9 | | | |

Table 2 summarizes two important trends that we observed with these analogs, being the single dose response comparison by aromatic substituent and position. Values shown in parentheses refer to the compound numbers as in Table 1.

TABLE 2

| | Meta - R$^2$ | Para - R$^3$ | Ortho - R$^1$ |
|---|---|---|---|
| Trifluoromethyl | 0.3 ± 0.6 (11) | 36.2 ± 0.9 (31) | 100.8 ± 1.9 (12) |
| Iodo | 8.6 ± 0.9 (29) | 32.7 ± 1.3 (3) | 68.4 ± 1.3 (26) |
| Chloro | 9.7 ± 0.9 (14) | 42.4 ± 0.9 (28) | 83.5 ± 8.2 (17) |
| Fluoro | 40.5 ± 1.0 (25) | 48.9 ± 1.1 (23) | 77.3 ± 1.6 (30) |
| Methoxy | 40.9 ± 1.3 (19) | 79.7 ± 0.9 (24) | 97.6 ± 1.8 (21) |

Thus, it can be seen that inhibition improves from ortho to para to meta substituent positions regardless of the substituent type. This suggests that meta substituents are preferred for steric, rather than electronic reasons. Second, in the meta-substituted series inhibition improves in the order of methoxy, fluoro, chloro, iodo, trifluoromethyl. This order reflects neither size nor electronic trends among these substituents. Five compounds (7, 11, 18, 29 and 31) were at least as potent as the lead compound (1). Three of the most potent compounds had one (11 and 31) or two (18) trifluoromethyl groups, consistent with the finding that this is the optimal substituent type among the meta series of monosubstituted analogs. In contrast to the improved inhibition observed when chlorine occupied both (1, K$_i$=1.6 µM) instead of only one (14, K$_i$=2.5 µM) of the meta positions, a single meta-trifluoromethyl (11, K$_i$=0.03 µM) was preferred over two (18, K$_i$=0.16 µM), Table 1. In fact, meta-trifluoromethyl (11) was 53-fold more potent than the lead compound while the disubstituted trifluoromethyl (18) was only 10-fold more potent than the lead. This suggests that one of the two meta substituents is located in a substantially larger pocket than the other.

These analogs from Tables 1 and 2 thus provided diverse substituent types and substitution patterns to serve as a training set suitable for specific activity prediction within this SAR series (as well as potential intermediate compounds for further reactions). The resulting analogs were examined for their ability to inhibit ATX-mediated hydrolysis of FS-3 at 10 µM. Likewise, each analog was tested in the presence of carboxyfluorescein (the product of ATX-mediated hydrolysis of FS-3) to identify false positive or negative results. None of the analogs tested significantly altered carboxyfluorescein fluorescence. Compounds containing meta substituents demonstrated responses in the range of 60% to 100% inhibition. Compound 11 with a trifluoromethyl group in the meta position, yielded 100% inhibition and was determined to be the best overall compound tested.

The selectivities of the inventive compounds (and ATX inhibitors) 3, 7, 11, 13, 14, 18, 19, 20, 22, 23, 25, 27, 28, 29 and 31, all of which inhibited ATX-mediated hydrolysis of FS-3 by ≧50% at single doses of 10 µM, were examined against NPP6 and NPP7 (in accordance with the test protocol provided above), the only other known lipid-preferring NPP isoforms. None of the compounds affected the activity of NPP6 or NPP7 (FIG. 6). Likewise, each analog was tested in the presence of p-nitrophenol (the product of ATX-mediated hydrolysis of p-nitrophenylphosphorylcholine (pNPPC)) to eliminate the chance of false positive or false negative results. None of the analogs tested had a significant affect on the p-nitrophenol absorbance. FIG. 3 provides a representation of the NPP6 and NPP7 single dose response plot. Columns in grey represent the isoform NPP6, columns in white represent the isoform NPP7 and the columns in black are p-nitrophenolate controls.

Figure 4:
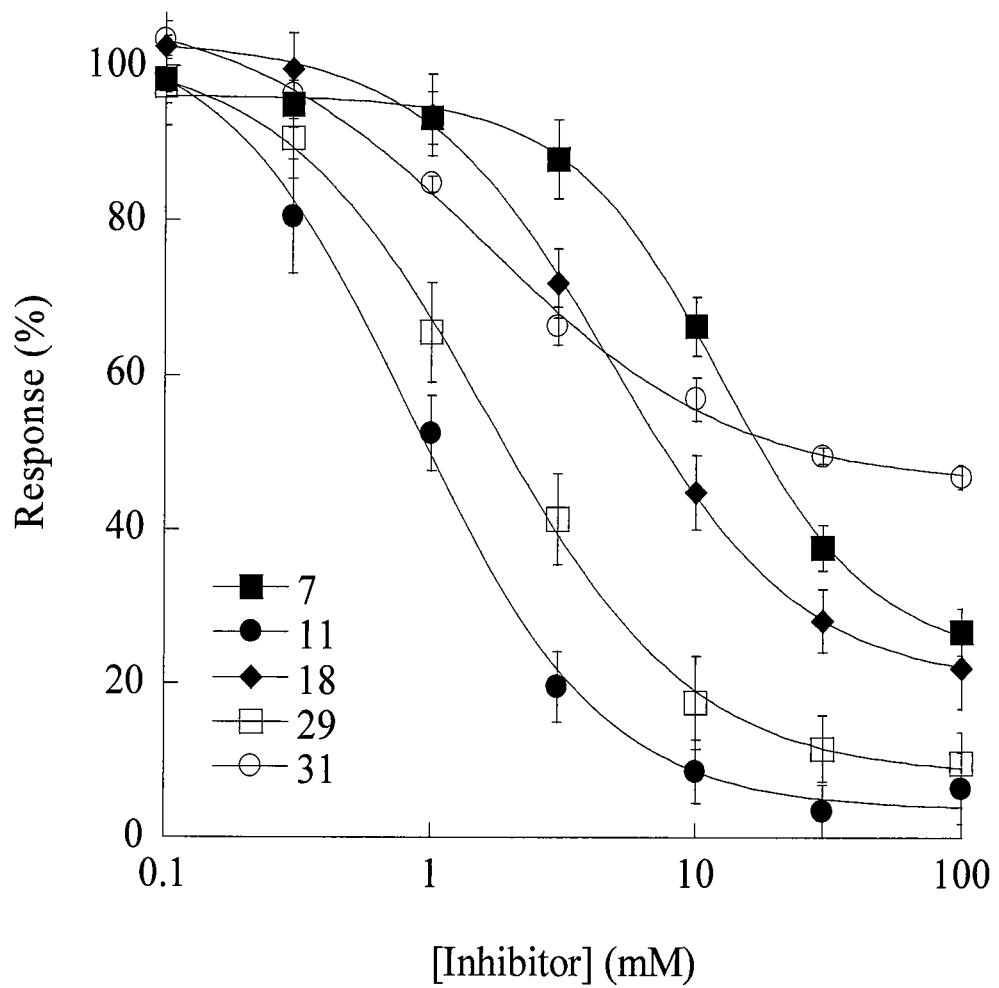
FIG. 4 is a graphical representation of autotaxin inhibition rates for representative inventive compounds.

In addition, dose-response curves were determined for all 15 analogs that inhibited ATX-mediated hydrolysis of FS-3 by ≧50% at 10 µM. $IC_{50}$ values in a range of 900 nM to 17.7 µM were observed (FIG. 7 and Table 1). Compounds demonstrating an $IC_{50}$ less than 15 µM were further examined to determine their mechanism of inhibition. From this data $K_i$ values were calculated for each analog and provided in the following Table and in the graph in FIG. 4.

| Substrate FS-3 (1 µM) | |
|---|---|
| Inhibitor | $IC_{50}$ (µM) |
| 7 | 12.1 |
| 11 | 0.9 ± 0.3 |
| 18 | 4.4 ± 1.5 |
| 29 | 1.6 |
| 31 | 1.5 |

These dose response plots show that these five inventive compounds are more potent than lead compound A, described above.

Thus, it is evident that the derivatization of pipemidic acid, such as with phenylthiourea reactants with various pendant groups (and some especially robust in ATX inhibition, as noted above) provides a viable manner of reacting autotaxin for inhibition of reactivity of such an enzyme. Tables 1 and 2 provide SAR insights, lead compound optimization data and mechanism of inhibition for the most potent analogs. Compounds 7, 11, and 18 were competitive ATX inhibitors with $K_i$ values ranging from 30 to 430 nM. Thus, these analogs are 3.7 to 53.3 times more potent than the lead. Compounds 29 and 31 were uncompetitive ATX inhibitors with $K_i$ values that were approximately equivalent to the lead. Finally, compounds 3, 13, 14, 20, 22, and 28 were mixed-mode ATX inhibitors with $K_i$ values ranging from 1.7 to 13.5 µM. Thus, these six analogs were as potent as or significantly less potent than the lead.

Thirty out of 70 potential analogs of compound 1 were synthesized based on binary QSAR predictions. These 30 analogs were characterized as ATX inhibitors using single dose screening, analysis of selectivity against other lipid preferring NPP isoforms, dose response determinations, and mechanism of inhibition analysis ($K_i$ determination). The fifteen analogs that inhibited ATX activity ≧50% were shown to be ATX selective. Eight analogs exhibited $IC_{50}$ for ATX-mediated FS-3 hydrolysis less than 10 µM. Five of these analogs exhibited either competitive or uncompetitive ATX inhibition with $K_i$ values ranging from 30 nM to 1.5 µM, which were significantly better than or equivalent to that of the lead. The best of these compounds has a potency approaching that reported for some of the most active published lipid-like ATX inhibitors.

As such, not only do some of these compounds demonstrate a significant advance in autotaxin inhibition, but the potential for further improvements in ATX inhibition methods may be available through the utilization of combinations of such compounds as well as further refinements and modifications of certain intermediate compounds as provided above.

Effects of Pipemidic Acid ATX Inhibitors on A2058 Cell Migration

A2058 cells were seeded in 96-well plates at a density of 50,000 cells per well in complete growth medium (DMEM+10% FBS+penicillin/streptomycin+L-glutamine). Cells were allowed to equilibrate for 24 hours at 37° C. with 5% $CO_2$. Cells were then serum-deprived for 24 hours in DMEM+0.1% BSA+penicillin/streptomycin+L-glutamine (serum-free medium). After 24 hours, the monolayer was scratched using a sterile 200 µl pipette tip, and each well was washed with 50 µl serum-free medium to remove damaged cells and treated with LPA 18:1 (10 µM), LPC 18:1 (10 µM), ATX (100 ng/ml), or a combination of LPC 18:1 and ATX in the presence and absence of pipemidic acid ATX inhibitors (30 µM). The width of the injury was measured at $T_0$, 4 hours (data not shown), 24 hours (data not shown), and 48 hours (shown above) after injury/treatment using the 10× objective of the phase-contrast microscope and the Micron USB software package. Data represent mean percent closure±SD. n=3 for each experiment. Data were analyzed using two-factor ANOVA with Bonferroni's post-test to determine if the pipemidic acid inhibitors significantly reduced cell migration versus vehicle control. *=p<0.05; **=p<0.01. These data indicate that 1 significantly inhibited both ATX- and LPC+ATX-stimulated migration in A2058 cells, after 48 hours. Additionally, 1 appeared to also reduce LPC-stimulated migration, although the reduction was not statistically significant. 20 and 14 also appeared to decrease LPC-, ATX-, and LPC+ATX-induced cell migration. However, these reductions were also not statistically significant.

Thus, Compound 1 shows statistically significant inhibition of cell migration stimulated by ATX/LPC co-treatment. This data demonstrate that the in vitro enzyme inhibition observed for this compound translates into a cellular assay system relevant to metastasis.

There are, of course, many alternative embodiments and modifications of the present invention which are intended to be included within the spirit and scope of this invention.

What we claim is:

1. A compound conforming to the following formula:

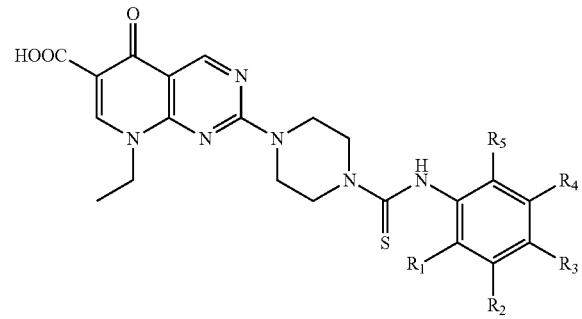

wherein $R_5$ is hydrogen; wherein $R_1$ may be selected individually from the group consisting of hydrogen and chloro; $R_2$ may be selected individually from the group consisting of hydrogen, halogen, methyl, methoxy, and trifluoromethyl; $R_3$ may be selected individually from the group consisting of hydrogen, halogen, trifluoromethyl, and methyl; $R_4$ may be selected individually from the group consisting of hydrogen, chloro, methyl, and trifluoromethyl; and wherein $R_2$ and $R_3$ may be combined to form a thiadiazole group, in which case $R_1$ and $R_4$ are hydrogen; wherein if $R_1$ is chloro, then $R_4$ is also chloro, and $R_2$ and $R_3$ are hydrogen; wherein if $R_2$ is halogen or methoxy, then $R_1$, $R_3$, and $R_4$ are hydrogen; wherein if $R_2$ is trifluoromethyl or methyl, then $R_1$ and $R_3$ are hydrogen and $R_4$ is either hydrogen or the same as $R_2$; wherein if $R_3$ is halogen, trifluoromethyl, or methyl, then $R_1$, $R_2$, and $R_4$ are hydrogen.

2. The compound of claim 1 wherein $R_2$ is trifluoromethyl and $R_1$, $R_3$, and $R_4$ are hydrogen.

3. The compound of claim 1 wherein $R_2$ and $R_4$ are trifluoromethyl and $R_1$ and $R_3$ are hydrogen.

4. The compound of claim 1 wherein $R_1$ and $R_4$ are chloro and $R_2$ and $R_3$ are hydrogen.

5. The compound of claim 1 wherein $R_2$ is halogen and $R_1$, $R_3$, and $R_4$ are hydrogen.

6. The compound of claim 5 wherein $R_2$ is iodo.

7. The compound of claim 5 wherein $R_2$ is chloro.

8. The compound of claim 1 wherein $R_2$ and $R_3$ combine to form dithiadiazole and $R_1$ and $R_4$ are hydrogen.

9. The compound of claim 1 wherein $R_2$ and $R_4$ are methyl and $R_1$ and $R_3$ are hydrogen.

10. The compound of claim 1 wherein $R_3$ is halogen and $R_1$, $R_2$, and $R_4$ are hydrogen.

11. The compound of claim 1 wherein $R_3$ is iodo.

12. The compound of claim 1 wherein $R_2$ and $R_4$ are trifluoromethyl and $R_1$ and $R_3$ are hydrogen.

13. The compound of claim 1 wherein $R_3$ is trifluoromethyl and $R_1$, $R_2$, and $R_4$ are hydrogen.

* * * * *